(12) United States Patent
Liaw

(10) Patent No.: US 8,367,797 B2
(45) Date of Patent: Feb. 5, 2013

(54) NITRO COMPOUND, AMINE COMPOUND AND POLYAMIDE DERIVED THEREFROM

(75) Inventor: Der-Jang Liaw, Taipei (TW)

(73) Assignee: National Taiwan University of Science and Technology, Taipei (TW)

( * ) Notice: Subject to any disclaimer, the term of this patent is extended or adjusted under 35 U.S.C. 154(b) by 149 days.

(21) Appl. No.: 12/806,902

(22) Filed: Aug. 23, 2010

(65) Prior Publication Data

US 2011/0275783 A1 Nov. 10, 2011

(30) Foreign Application Priority Data

May 4, 2010 (TW) .............................. 99114191 A

(51) Int. Cl.
*C08G 69/26* (2006.01)
(52) U.S. Cl. ......... 528/342; 567/157; 564/306; 564/326
(58) Field of Classification Search .................. 528/342; 567/157; 564/306, 326
See application file for complete search history.

(56) References Cited

U.S. PATENT DOCUMENTS 6,137,008 A * 10/2000 Liaw et al. .................... 564/315

OTHER PUBLICATIONS

Chang et al., Polymer 51 (2010), 44-3-4502.*

* cited by examiner

*Primary Examiner* — Shane Fang
(74) *Attorney, Agent, or Firm* — J.C. Patents

(57) ABSTRACT

A polyamide represented by formula (6) is provided. The polyamide is fabricated by performing a polycondensation reaction with amine compound shown in formula (4) and an acid or derivative thereof shown in formula (5) as monomers. In formulas (5) and (6), X represents aromatic groups or aliphatic groups. In formula (5), R represents OH group or halogen.

3 Claims, 12 Drawing Sheets
(3 of 12 Drawing Sheet(s) Filed in Color)

NITRO COMPOUND, AMINE COMPOUND AND POLYAMIDE DERIVED THEREFROM

CROSS-REFERENCE TO RELATED APPLICATION

This application claims the priority benefit of Taiwan application serial no. 99114191, filed on May 4, 2010. The entirety of the above-mentioned patent application is hereby incorporated by reference herein and made a part of this specification.

BACKGROUND OF THE INVENTION

1. Field of the Invention

The invention relates to a nitro compound, an amine compound, and a polyamide. More particularly, the invention relates to a new nitrophenyl compound containing a triphenylamide group, a new phenylamine compound fabricated with the nitrophenyl compound, a new dinitro compound fabricated with the phenylamine compound, a new diamine compound fabricated with the dinitro compound, and a new polyamide fabricated by using the aforementioned diamine compound with an acid or an acid derivative.

2. Description of Related Art

As polyamide (PA) can be applied in gas-gas separation, liquid-liquid separation, and gas-liquid separation thin films, these PA thin films become essential in the era promoting energy saving and new energy development. Usually, PA can be fabricated into reinforced PA composite material with conventional fiber and inorganic filler. Moreover, PA can also be fabricated into PA with high performance and high strength through the interaction between PA and metal ions. In other words, by utilizing the technique of modifying PA, PA with superior heat-resistance, weather-resistance, flame-resistance, flexibility, elasticity, and size stabilizing enhancement is fabricated.

Although PA has superior heat-resistance and mechanical characteristics, the problem of unfavorable processability is usually present. Moreover, PA has high melting point or softening point, and therefore can not be processed by heating and melting. In addition, PA has low solubility, and therefore can not be processed to form by dissolving in solvents. Hence, most of aromatic PAs have difficulties in the formation processing.

SUMMARY OF THE INVENTION

Accordingly, the invention is directed to a nitro compound, an amine compound, and a polyamide derived therefrom. The foregoing polymers contain triphenylamide and therefore have superior solubility, high glass transition temperature, high thermal stability, and have electrochemical properties and electrochromic properties.

A nitro compound is provided in the invention. The nitro compound is a nitrophenyl compound of 4,4'-di-isopropylphenyl-4''-nitrotriphenyl-amine (DIPNTPA) represented by Formula (1).

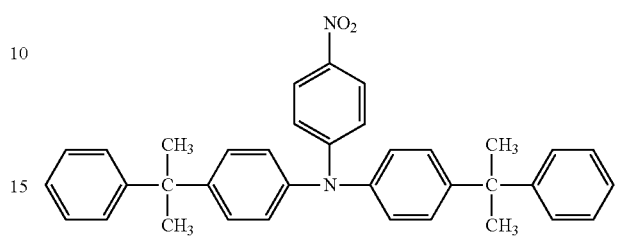

Formula (1)

An amine compound is provided in the invention. The amine compound is a phenylamine compound of 4-amino-4',4''-di-isopropylphenyl-triphenylamine (ADIPTPA), fabricated by using the nitro compound represented in Formula (1) as a monomer. The amine compound is represented by Formula (2).

Formula (2)

A nitro compound is provided in the invention. The nitro compound is a dinitro compound of N,N-bis(4-diisopropylphenyl)-N',N'-bis(4-nitrophenyl)-1,4-phenylenediamine (BDBNPD), fabricated by using the amine compound represented in Formula (2) as a monomer. The nitro compound is represented by Formula (3).

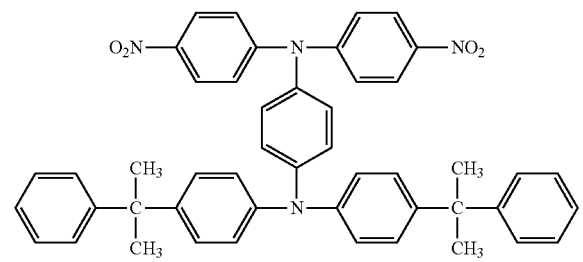

Formula (3)

An amine compound is provided in the invention. The amine compound is a diamine compound of N,N-bis(4-aminophenyl)-N',N'-bis(4-diisopropylphenyl)-1,4-phenylenediamine (BABDPD), fabricated by using the nitro compound represented in Formula (3) as a monomer. The amine compound is represented by Formula (4).

Formula (4)

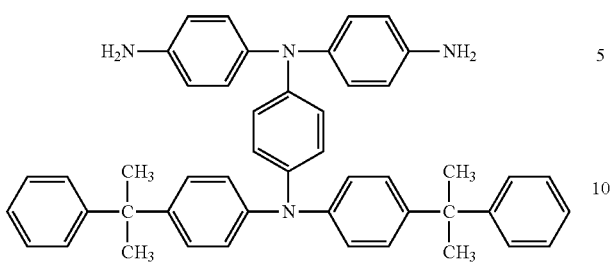

A polyamide is provided in the invention. The polyamide is fabricated by performing a polycondensation reaction with the amine compound represented in Formula (4) and an acid or an acid derivative represented in Formula (5) as monomers. The polyamide is represented by Formula (6).

Formula (5)

ROC—X—COR

Formula (6)

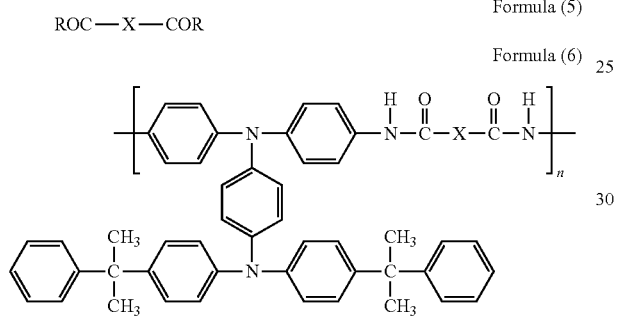

In Formulae (5) and (6), X represents an aromatic group or an aliphatic group.

According to an embodiment of the invention, in Formulae (5) and (6), X represents a group selected from Formulae (5-1) to (5-11).

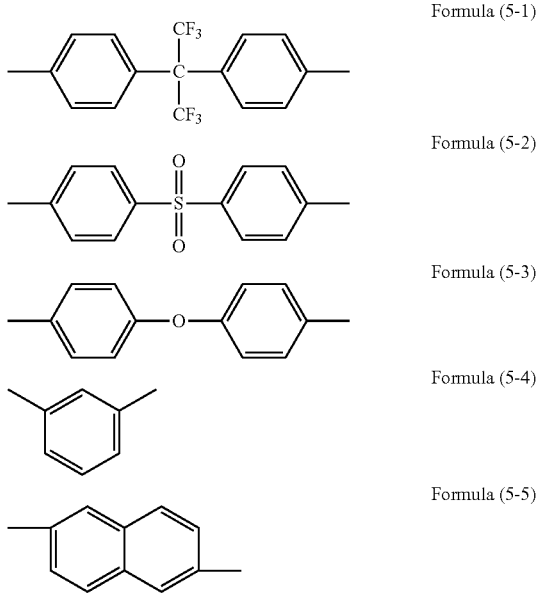

Formula (5-1)

Formula (5-2)

Formula (5-3)

Formula (5-4)

Formula (5-5)

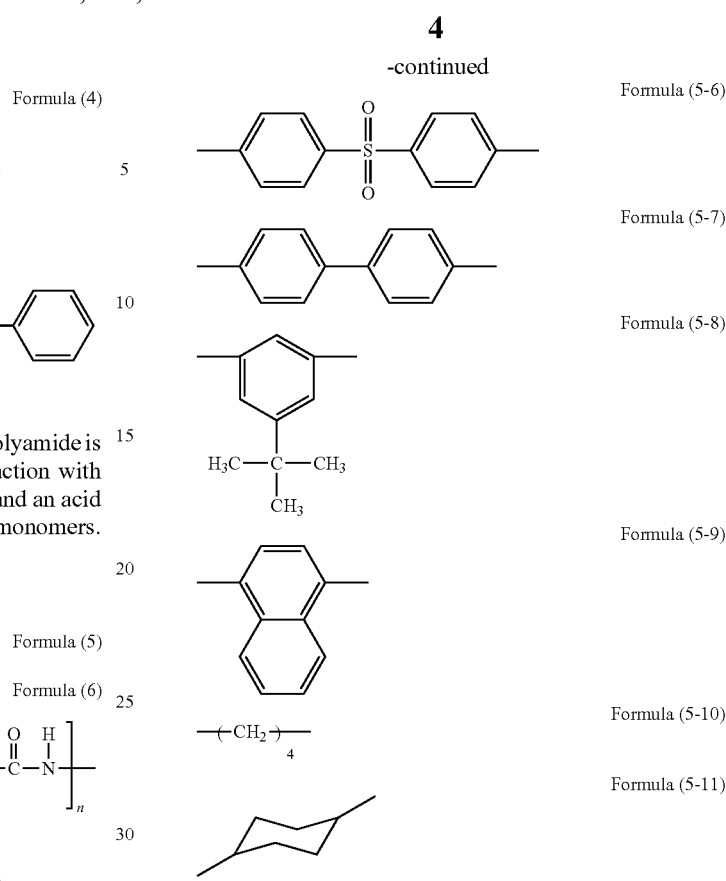

Formula (5-6)

Formula (5-7)

Formula (5-8)

Formula (5-9)

Formula (5-10)

Formula (5-11)

According to an embodiment of the invention, in Formula (5), R represents an OH group or a halogen. The halogen, for example, is chlorine.

In light of the foregoing, the technical feature of the invention includes a new nitrophenyl compound containing a triphenylamine group, a new phenylamine compound fabricated with the nitrophenyl compound, a new dinitro compound fabricated with the phenylamine compound, a new diamine compound fabricated with the dinitro compound, and a new polyamide fabricated with the aforementioned diamine compound and an acid or an acid derivative. The new polyamide contains a bis-triphenylamide group and thus has superior solubility, high glass transition temperature, and thermal stability. Consequently, the processability of polyamide can be improved to enhance the application thereof. Furthermore, the new polyamide also has electrochemical properties and electrochromic properties.

In order to make the aforementioned and other features and advantages of the invention more comprehensible, several embodiments accompanied with figures are described in detail below.

BRIEF DESCRIPTION OF THE DRAWINGS

The patent or application file contains at least one drawing executed in color. Copies of this patent or patent application publication with color drawings will be provided by the Office upon request and payment of the necessary fee. The accompanying drawings are included to provide a further understanding of the invention, and are incorporated in and constitute a part of this specification. The drawings illustrate embodiments of the invention and, together with the description, serve to explain the principles of the invention.

DESCRIPTION OF EMBODIMENTS

In the following, the technical features of the invention including a new nitrophenyl compound containing a triphenylamide group, a new phenylamine compound fabricated with the nitrophenyl compound, a new dinitro compound fabricated with the phenylamine compound, a new diamine compound fabricated with the dinitro compound, and a new polyamide fabricated with the aforementioned diamine and an acid or an acid derivative are provided.

I. Nitrophenyl Compound

A nitro compound of an embodiment of the invention is a nitrophenyl compound of 4,4'-di-isopropyl-phenyl-4"-nitrotriphenylamine (DIPNTPA), as illustrated in Formula (1). Moreover, DIPNTPA contains triphenylamide.

Formula (1)

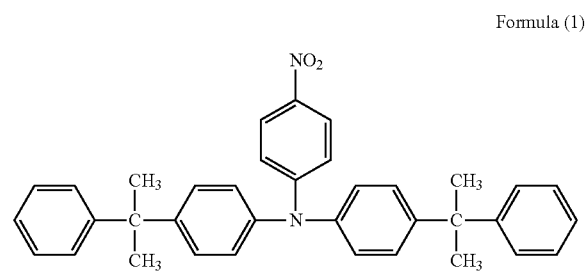 [SMILES: CC(C)(c1ccccc1)c1ccc(N(c2ccc([N+](=O)[O-])cc2)c2ccc(C(C)(C)c3ccccc3)cc2)cc1]

Thereafter, a method of synthesizing DIPNTPA is illustrated with an example. The chemical structure of a compound fabricated is further identified and analyzed.

Firstly, 49 milli-mole (mmole) of bis[4-(2-phenyl-2-propyl)phenylamine], 49 mmole of 1-fluoro-4-nitrobenzene, 49 mmole of sodium hydride, and 120 milli-liter (ml) of dimethyl sulfoxide are placed in a reaction vessel and reacted for 48 hours at 120° C. to obtain a reaction mixture. Next, the cooled reaction mixture is precipitated in methanol to obtain the solid portion. Afterwards, a yellow solid, that is, DIPNTPA, is obtained from the solid portion by column chromatography with a solvent ratio of n-hexane:dichloromethane=2:1. DIPNTPA has a measured melting point of 150-151° C. and a production yield of 50%.

A synthetic reaction of DIPNTPA aforementioned is shown in the following.

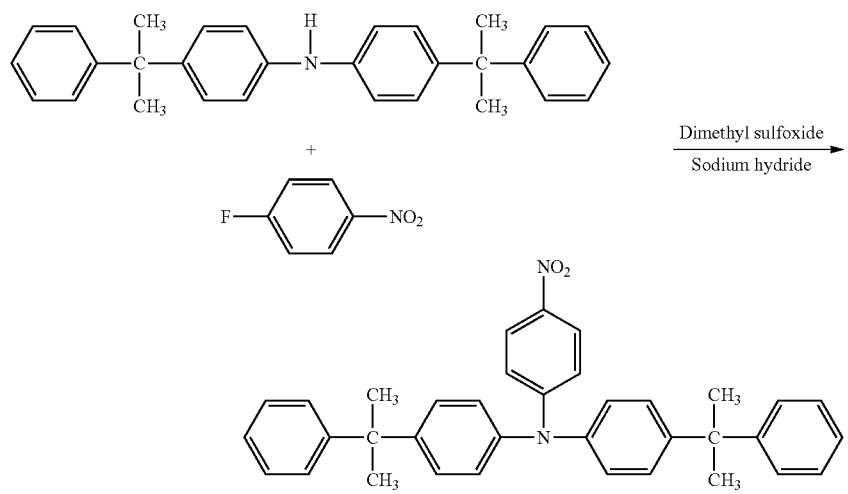

Figure 1:
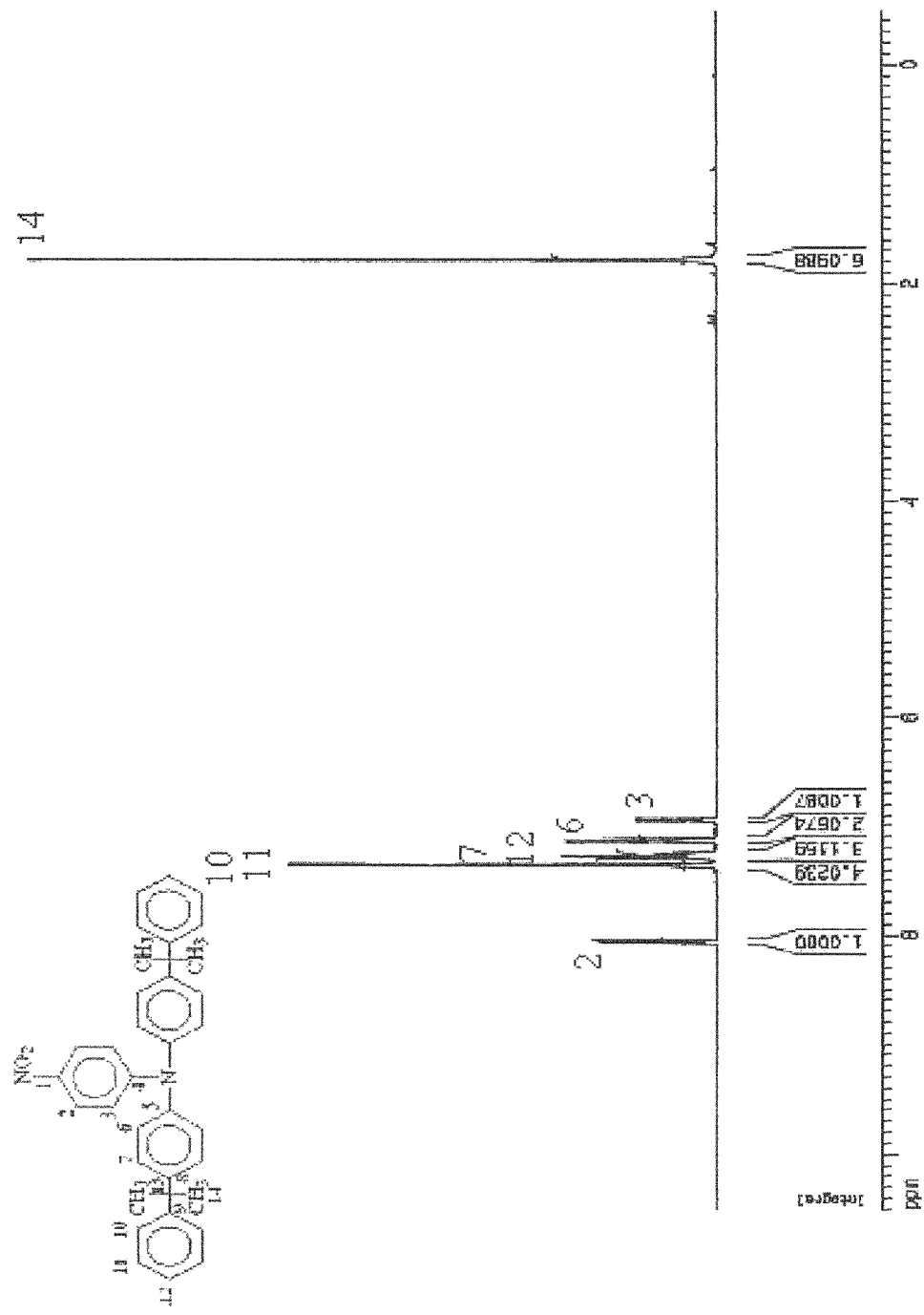
FIGS. 1 and 2 respectively illustrate schematic nuclear magnetic resonance (NMR) spectrums of $^1$H-NMR and $^{13}$C-NMR of a DIPNTPA nitrophenyl compound according to an embodiment of the invention.
Figure 2:
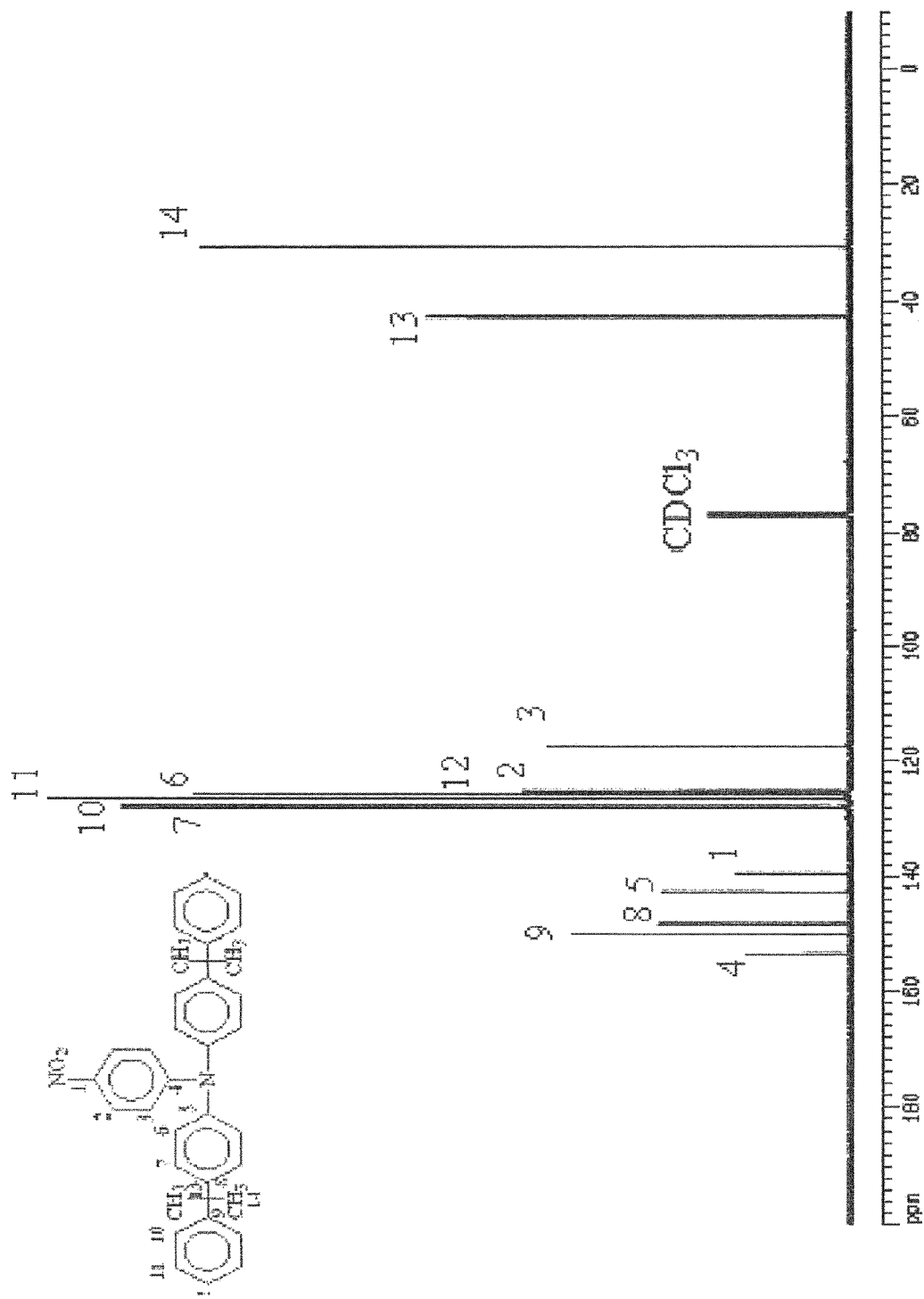

In addition, DIPNTPA obtained is identified by using a $^1$H-NMR analysis and a $^{13}$C-NMR analysis of a nuclear magnetic resonance spectrum (NMR spectrum) and an element analysis. FIGS. 1 and 2 respectively illustrate schematic nuclear magnetic resonance spectrums of $^1$H-NMR and $^{13}$C-NMR of a DIPNTPA nitrophenyl compound according to an embodiment of the invention. In the NMR spectrums shown in FIGS. 1 and 2, s represents a singlet, d represents a doublet, t represents a triplet, q represents a quartet, and m represents a multiplet.

$^1$H NMR (CDCl$_3$): δ (ppm)=8.05-8.08 (d, 1H); 7.37-7.38 (d, 2H); 7.35-7.36 (t, 2H); 7.28-7.30 (d, 2H); 7.24-7.27 (m, 1H); 7.12-7.14 (d, 2H); 6.93-6.95 (d, 1H); 1.78 (s, 6H).

$^{13}$C NMR (CDCl$_3$): δ (ppm)=153.46, 150.01, 148.26, 142.80, 139.62, 128.13, 128.03, 126.62, 125.88, 125.71, 125.31, 117.42, 42.62, 30.65.

The element analysis result of DIPNTPA of the present embodiment is presented below. Theoretical values are: C, 82.10%; H, 6.51%; N, 5.32%. Analytical values are: C, 81.67%; H, 6.39%; N, 5.21%.

II. Phenylamine Compound

An amine compound of an embodiment of the invention is a phenylamine compound of 4-amino-4',4"-di-isopropylphenyl-triphenylamine (ADIPTPA), as illustrated in Formula (2). Moreover, ADIPTPA contains triphenylamide.

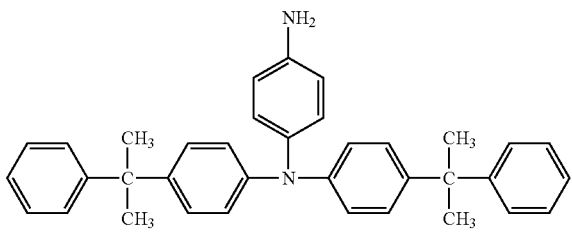

Formula (2)

Next, a method of fabricating ADIPTPA is illustrated with an example. A chemical structure of a compound fabricated is further identified and analyzed.

Firstly, 33.46 mmole of DIPNTPA monomer, 0.3 gram (g) of 10% Pd/C, and 200 ml of ethanol are placed in a reaction vessel. The mixture is heated to 90° C., and 10 ml of hydrazine (H$_2$NNH$_2$.H$_2$O) is then slowly added into the mixture. After hydrazine has been added, the mixture is reacted for 24 hours. Upon completion of the reaction, the mixture is filtered while still hot so that the 10% Pd/C is removed and the filtered solution is obtained. After the filter solution obtained is cooled and precipitated, another filtration is performed to obtain the solid portion. The solid obtained is then crystallized twice with ethanol so as to obtain a white amine compound. The white amine compound is dried under a vacuum environment. ADIPTPA has a measured melting point of 107-108° C. and a production yield of 60%.

A synthetic reaction of ADIPTPA aforementioned is shown in the following:

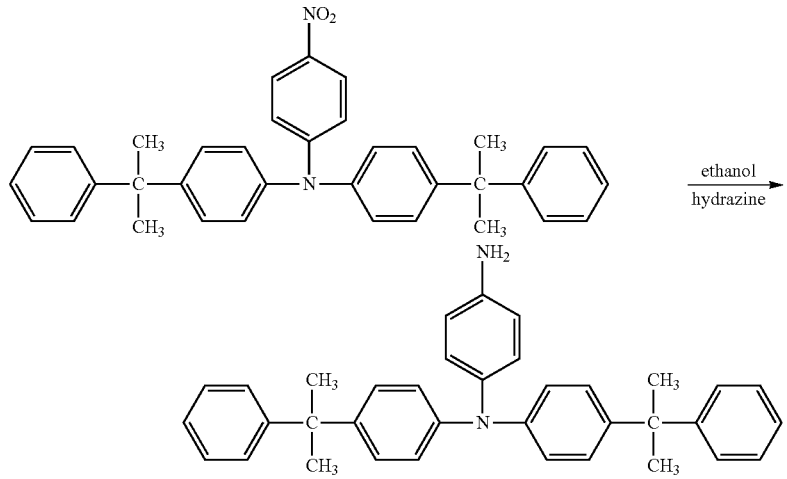

Figure 3:
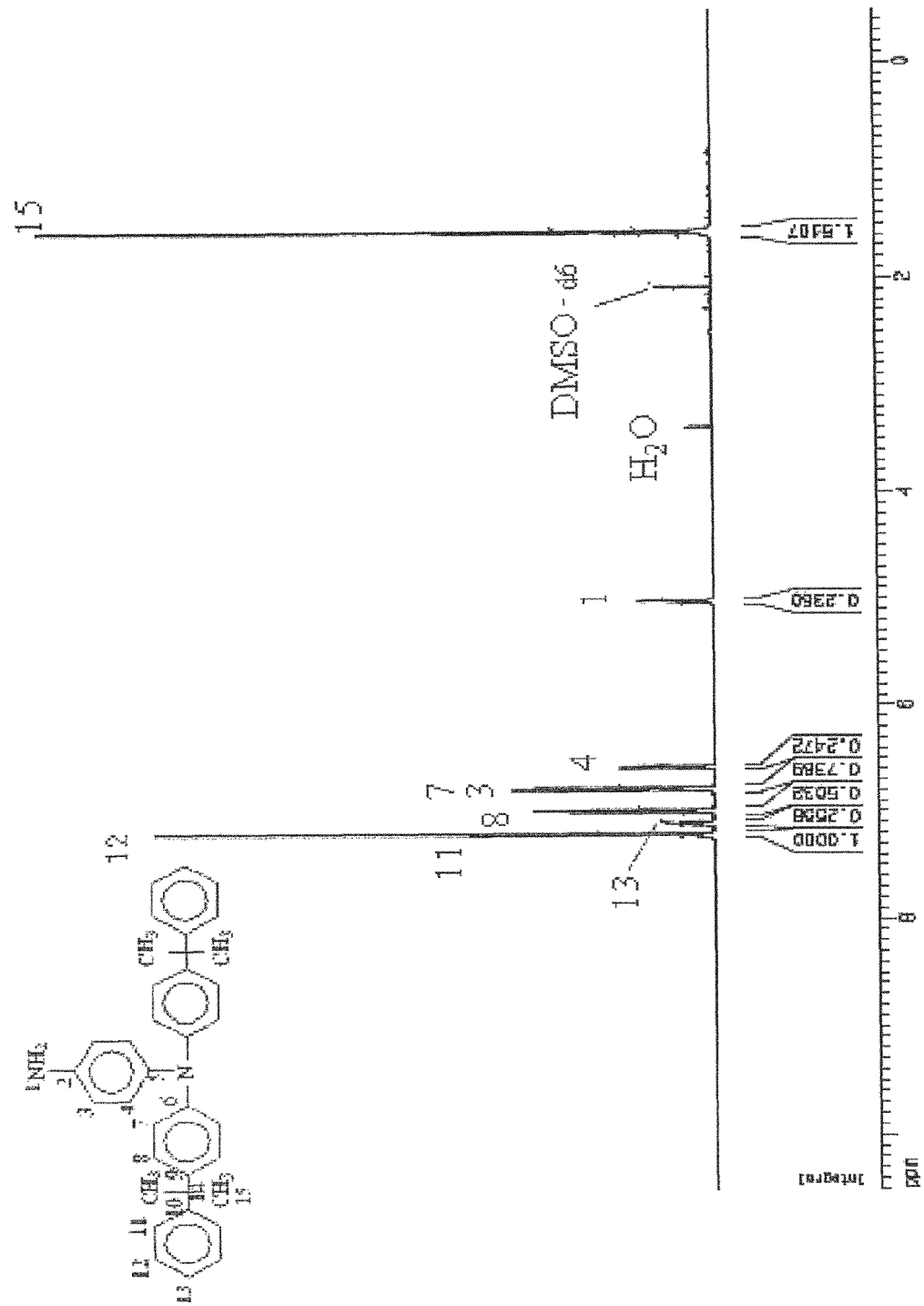
FIGS. 3 and 4 respectively illustrate schematic NMR spectrums of $^1$H-NMR and $^{13}$C-NMR of an ADIPTPA phenylamine compound according to an embodiment of the invention.
Figure 4:
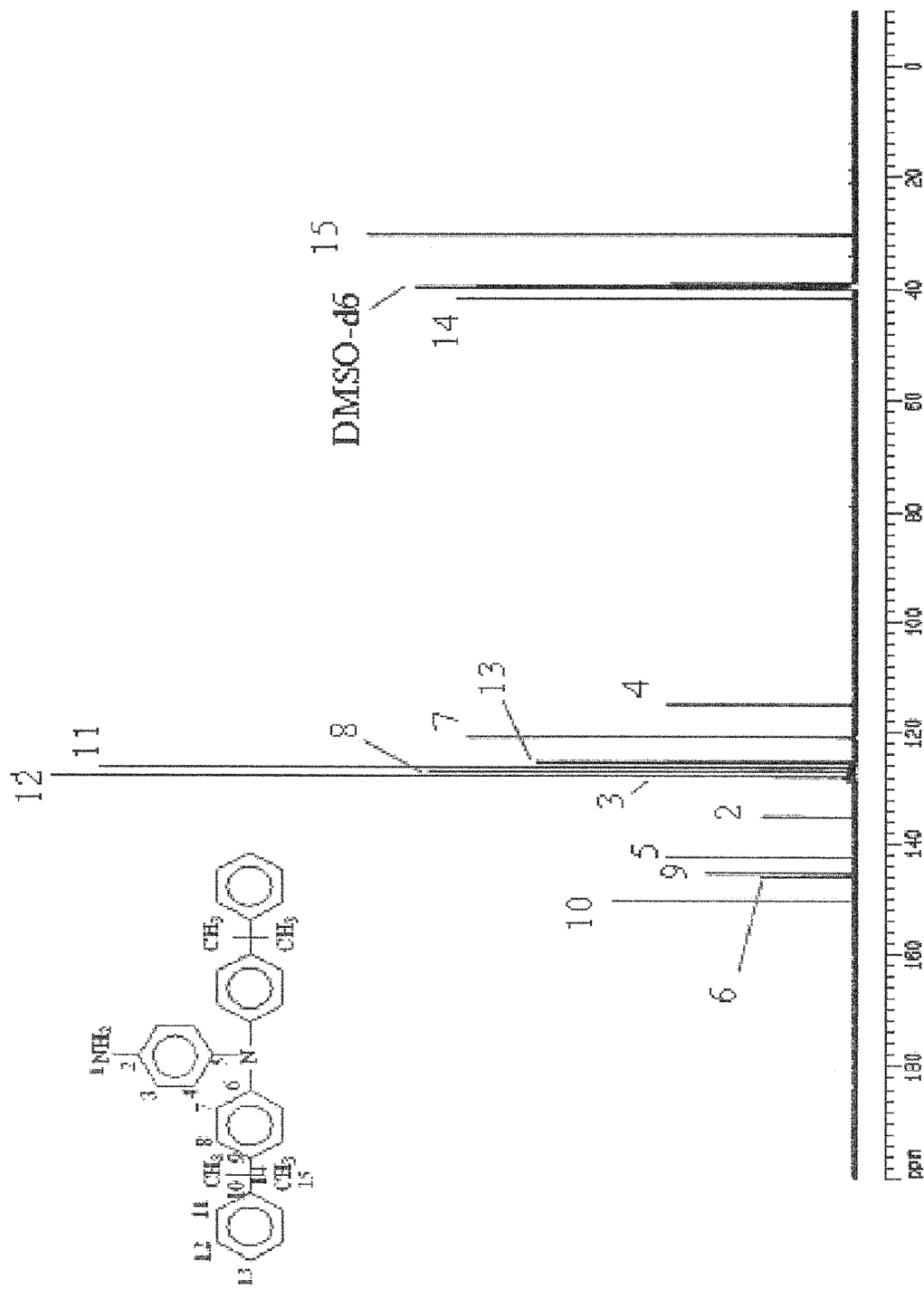

In addition, ADIPTPA obtained is identified by using the $^1$H-NMR analysis and the $^{13}$C-NMR analysis of the NMR spectrum and the element analysis. FIGS. 3 and 4 respectively illustrate schematic NMR spectrums of $^1$H-NMR and $^{13}$C-NMR of an ADIPTPA phenylamine compound according to an embodiment of the invention. In the NMR spectrums shown in FIGS. 3 and 4, s represents a singlet, d represents a doublet, t represents a triplet, q represents a quartet, and m represents a multiplet.

$^1$H NMR (DMSO-d$_6$): δ (ppm)=7.20-7.21 (d, 2H); 7.19-7.20 (d, 2H); 7.09-7.12 (m, H); 6.98-7.00 (d, 2H); 6.79 (d, 2H); 6.77 (d, 2H); 6.56-6.58 (d, 1H); 5.02 (s, 1H); 1.57 (s, 6H).

$^{13}$C NMR (DMSO-d$_6$): δ (ppm)=150.3, 145.9, 145.4, 142.5, 135.2, 125.3, 127.9, 127.8, 126.9, 126.2, 125.3, 120.73, 114.9, 41.7, 30.3.

The element analysis result of ADIPTPA of the present embodiment is presented below. Theoretical values are: C, 87.05%; H, 7.31%; N, 5.64%. Analytical values are: C, 86.90%; H, 7.13%; N, 5.61%.

III. Dinitro Compound

A nitro compound of an embodiment of the invention is a dinitro compound of N,N-bis(4-diisopropylphenyl)-N',N'-bis(4-nitrophenyl)-1,4-phenylenediamine (BDBNPD), as illustrated in Formula (3). Moreover, BDBNPD contains bis-triphenylamine.

Formula (3)

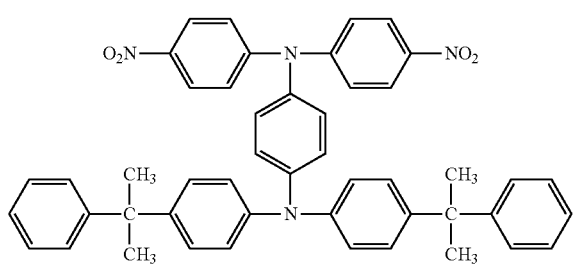

Thereafter, a synthetic method of BDBNPD is illustrated with an example. A chemical structure of a compound fabricated is further identified and analyzed.

Firstly, 14.63 mmole of ADIPTPA, 29.27 mmole of 1-fluoro-4-nitrobenzene, 29.27 mmole of cesium fluoride, and 80 ml of dimethyl sulfoxide are placed in a reaction vessel and reacted for 24 hours at 120° C. The cooled reaction mixture is then precipitated in methanol to obtain the solid portion. Afterwards, a yellow solid, that is, BDBNPD, is obtained from the solid portion by column chromatography with a solvent ratio of n-hexane:dichloromethane=1:1. This BDBNPD has a measured melting point of 224-225° C. and a production yield of 50%.

A synthetic reaction of BDBNPD aforementioned is shown in the following:

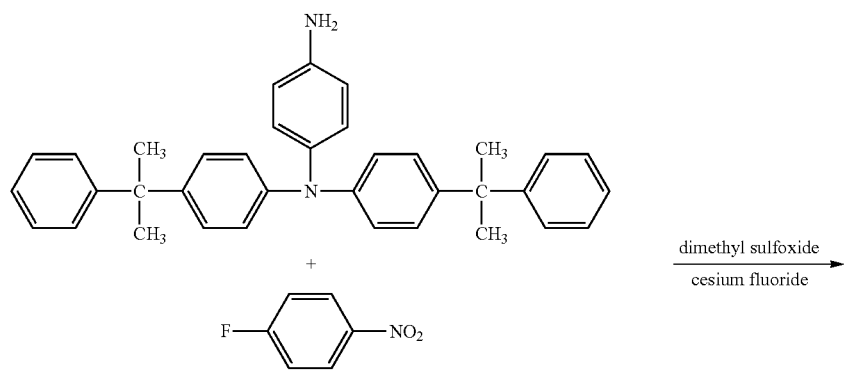

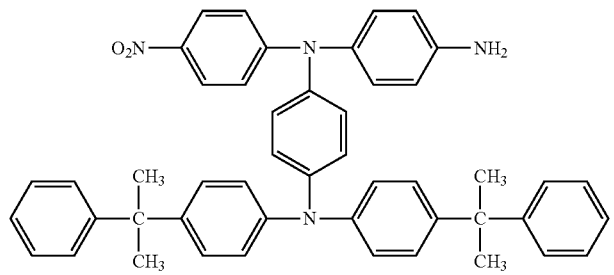

Figure 5:
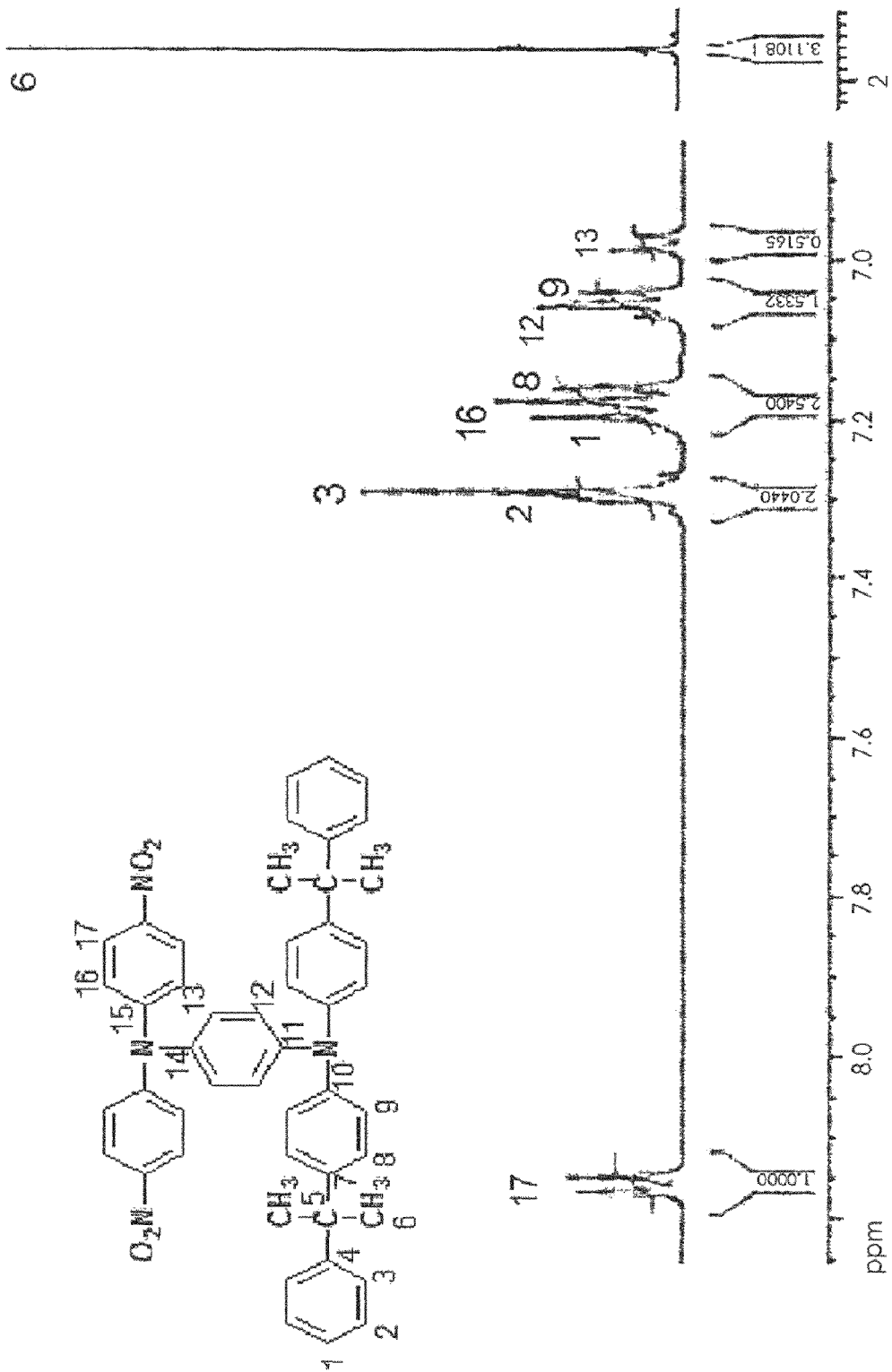
FIGS. 5 and 6 respectively illustrate schematic NMR spectrums of $^1$H-NMR and $^{13}$C-NMR of a BDBNPD dinitro compound according to an embodiment of the invention.
Figure 6:
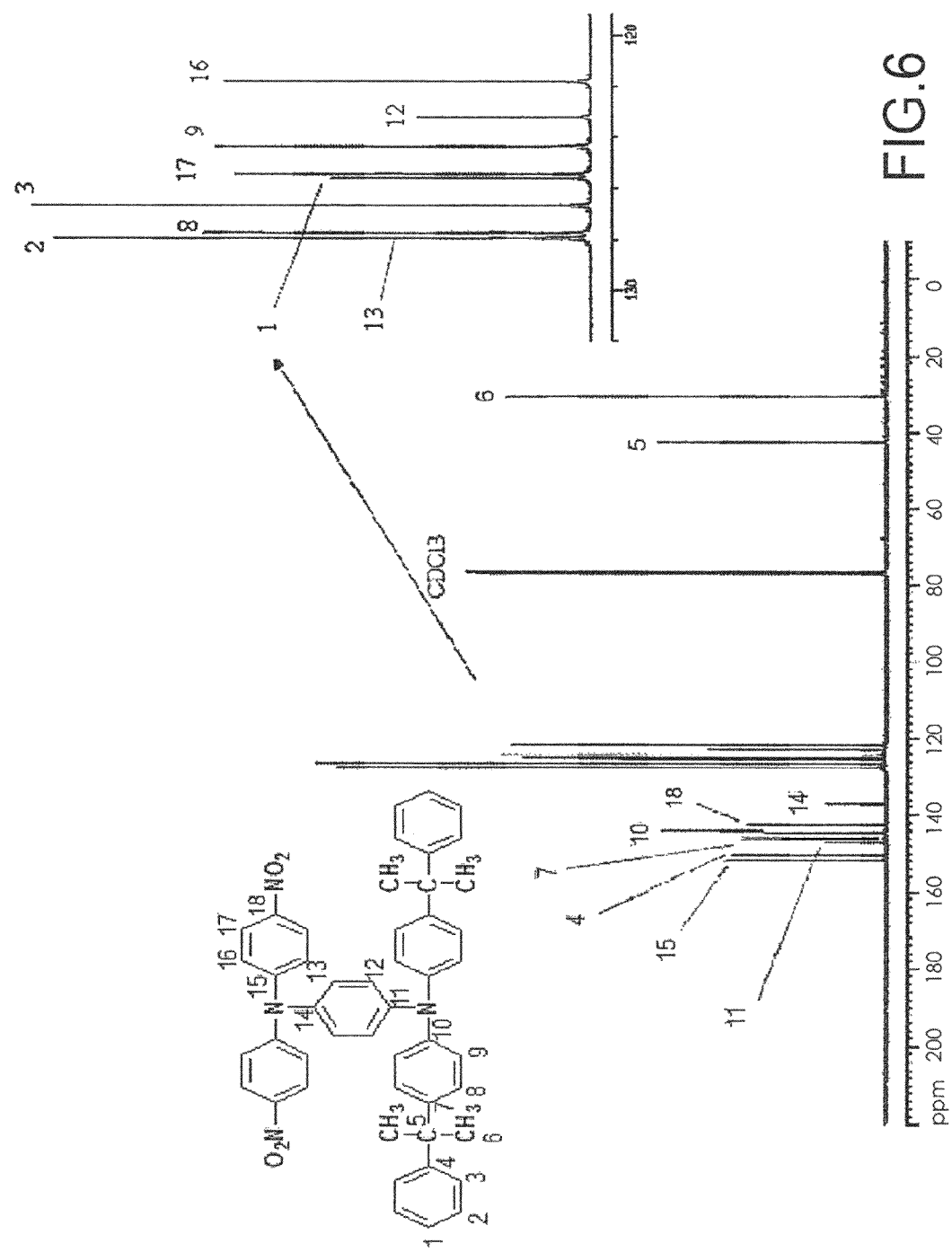

In addition, BDBNPD obtained is identified by using the $^1$H-NMR analysis and the $^{13}$C-NMR analysis of the NMR spectrum and the element analysis. FIGS. 5 and 6 respectively illustrate schematic NMR spectrums of $^1$H-NMR and $^{13}$C-NMR of a BDBNPD dinitro compound according to an embodiment of the invention. In the NMR spectrums shown in FIGS. 5 and 6, s represents a singlet, d represents a doublet, t represents a triplet, q represents a quartet, and m represents a multiplet.

$^1$H-NMR (CDCl$_3$): δ (ppm)=8.14-8.17 (d, 2H); 7.30-7.31 (t, 2H); 7.28-7.29 (d, 2H); 7.21 (m, 1H); 7.17-7.19 (d, 2H); 7.15-7.17 (d, 2H); 7.05-7.07 (d, 2H); 7.04-7.05 (d, 2H); 6.97-6.98 (d, 2H); 1.70 (s, 6H, Hd).

$^{13}$C NMR (CDCl$_3$): δ (ppm)=151.7, 150.4, 147.0, 146.1, 144.3, 142.3, 137.2, 127.96, 127.94, 127.7, 126.6, 125.6, 125.4, 124.3, 123.2, 121.8, 42.5, 30.7.

The element analysis result of BDBNPD of the present embodiment is presented below. Theoretical values are: C, 78.03%; H, 5.73%; N, 7.58%. Analytical values are: C, 77.57%; H, 5.63%; N, 7.45%.

IV. Diamine Compound

An amine compound of an embodiment of the invention is a diamine compound of N,N-bis(4-aminophenyl)-N',N'-bis (4-diisopropylphenyl)-1,4-phenylenediamine (BABDPD), as illustrated in Formula (4). Moreover, BABDPD contains bis-triphenylamine.

Formula (4)

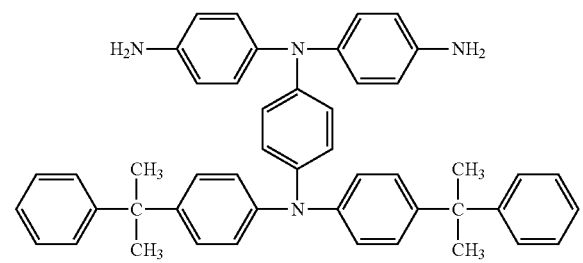

Next, a method of fabricating BABDPD is illustrated with an example. A chemical structure of a compound fabricated is further identified and analyzed.

Firstly, 4.1 mmole of BDBNPD monomer, 0.1 gram of 10% Pd/C, and 120 ml of ethanol are placed in a reaction vessel. The mixture is heated to 90° C., and 3 ml of hydrazine is then slowly added into the mixture. After hydrazine has been added, the mixture is reacted for 24 hours. Upon completion of the reaction, the mixture is filtered while still hot so that the 10% Pd/C is removed and the filtered solution is obtained. After the filter solution obtained is cooled and precipitated, another filtration is performed to obtain the solid portion. A pink diamine compound is obtained from the solid portion by using column chromatography with a solvent ratio of ethyl acetate:n-hexane=1:3. The pink diamine compound is then dried under a vacuum environment. BABDPD has a measured melting point of 200-201° C. and a production yield of 60%.

A synthetic reaction of BABDPD aforementioned is shown in the following:

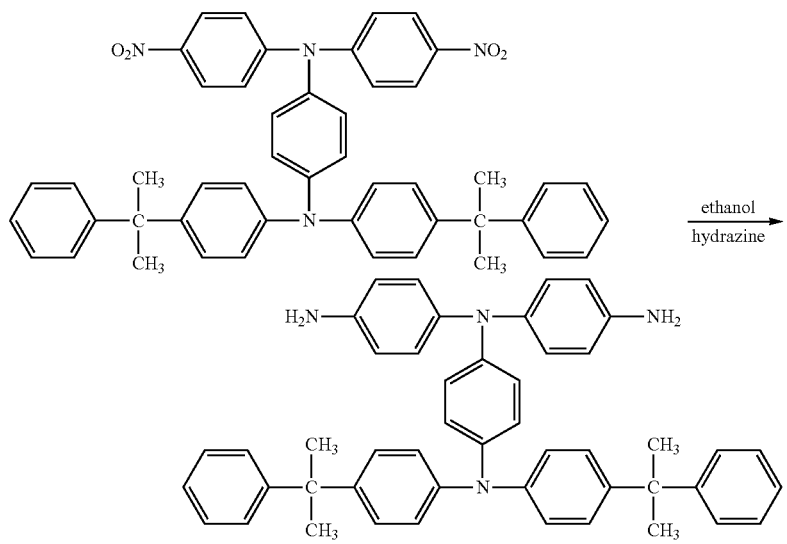

Figure 7:
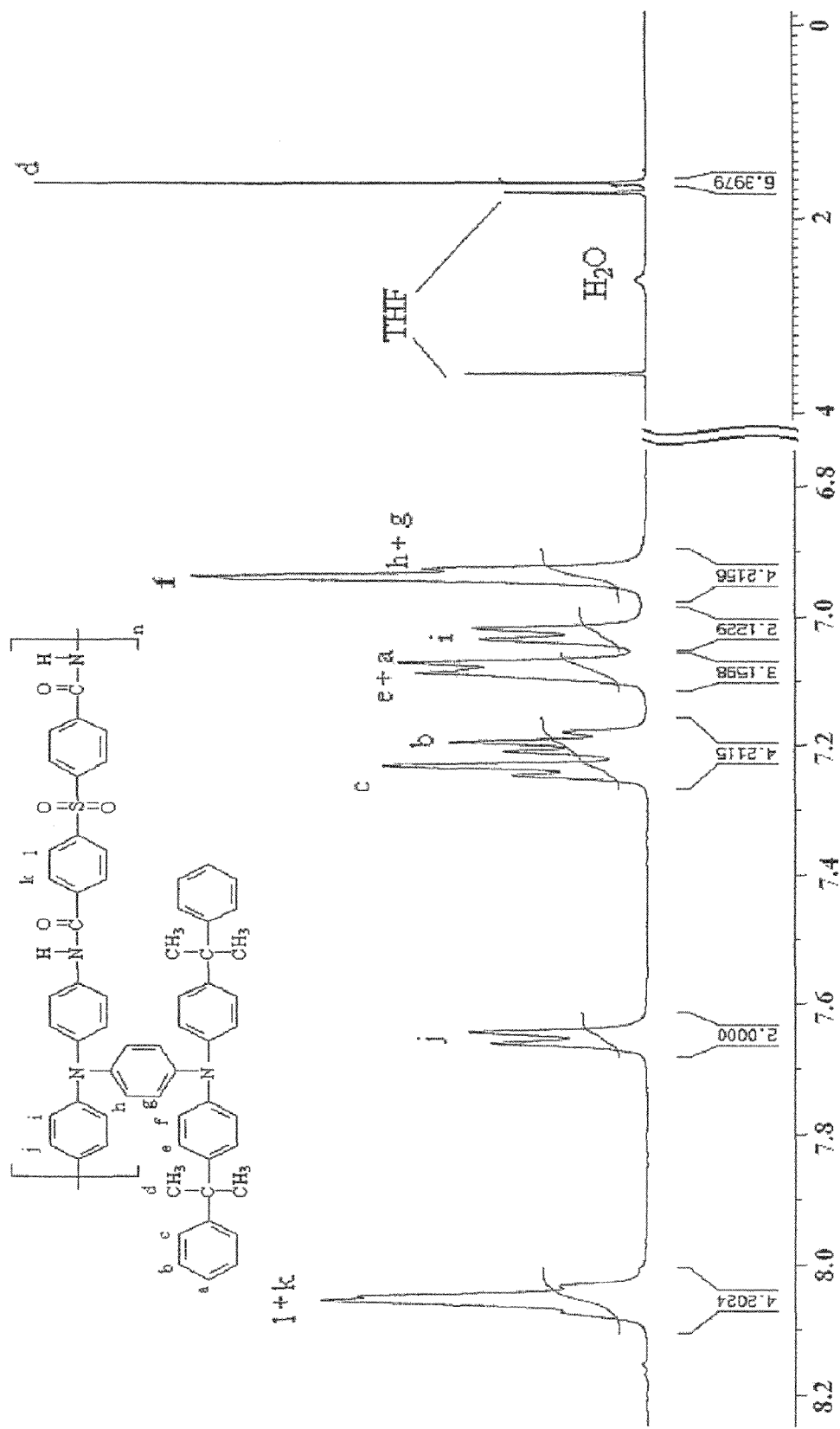
FIG. 7 illustrates a schematic NMR spectrum of $^1$H-NMR of a BABDPD diamine compound according to an embodiment of the invention.

In addition, BABDPD is identified by using the $^1$H-NMR analysis and the $^{13}$C-NMR analysis of the NMR spectrum and the element analysis. FIG. 7 illustrates a schematic NMR spectrum of $^1$H-NMR of a BABDPD diamine compound according to an embodiment of the invention. In the NMR spectrum shown in FIG. 7, s represents a singlet, d represents a doublet, t represents a triplet, q represents a quartet, and m represents a multiplet.

$^1$H NMR (DMSO-d$_6$): δ (ppm)=7.21-7.23 (d, H); 7.19-7.20 (d, 2H); 7.09-7.12 (s, 6H); 6.99-7.01 (d, 2H); 6.80-6.82 (d, 2H); 6.77-6.78 (d, 2H); 6.75-6.77 (d, 1H); 6.56-6.58 (d, 2H); 6.53-6.54 (d, H, He); 4.93 (s, 1H); 1.56 (s, 6H, Hd).

$^{13}$C NMR (DMSO-d$_6$): δ (ppm)=150.2, 146.2, 145.3, 145.2, 143.0, 137.25, 136.0, 127.8, 127.1, 127.0, 126.7, 126.3, 125.3, 121.3, 117.8, 114.8, 41.7, 30.4.

The element analysis result of BABDPD of the present embodiment is presented below. Theoretical values are: C, 84.92%; H, 6.83%; N, 8.25%. Analytical values are: C, 84.11%; H, 6.77%; N, 8.17%.

V. Polyamide

A polyamide of an embodiment of the invention has a structure as shown in Formula (6). The polyamide is fabricated by performing a polycondensation reaction with BABDPD represented by Formula (4) and the acid or the acid derivative represented by Formula (5) as monomers.

ROC—X—COR   Formula (5)

Formula (6)

[structure: polyamide repeat unit with BABDPD-derived diamine and X linker]

In Formulae (5) and (6), X represents an aromatic group or an aliphatic group. Moreover, the new polyamide is derived from the BABDPD diamine compound as illustrated in Formula (4), and therefore includes bis-triphenylamine.

In one embodiment, X in Formulae (5) and (6) is a group illustrated in Formula (5-1), Formula (5-2), Formula (5-3), Formula (5-4), Formula (5-5), Formula (5-6), Formula (5-7), Formula (5-8), Formula (5-9), Formula (5-10), or Formula (5-11).

Formula (5-1): [4,4'-hexafluoroisopropylidene-diphenylene]

Formula (5-2): [4,4'-sulfonyldiphenylene]

Formula (5-3): [4,4'-oxydiphenylene]

Formula (5-4): [1,3-phenylene]

Formula (5-5): [2,6-naphthylene]

Formula (5-6): [3,3'-sulfonyldiphenylene]

Formula (5-7): [4,4'-biphenylene]

Formula (5-8): [5-(2-phenylpropan-2-yl)-1,3-phenylene / isopropylidene-substituted phenylene]

Formula (5-9): [1,5-naphthylene]

Formula (5-10): $-(CH_2)_4-$

Formula (5-11): [cyclohexylene]

Furthermore, in one embodiment, R in Formula (5) is an OH group or a halogen, in which the halogen is chlorine, for example. Specifically, the acid or the acid derivative shown in Formula (5), for instance, is the diacid compound as illustrated in Formula (7) or the diacyl chloride compound as illustrated in Formula (8).

HOOC—X—COOH   Formula (7)

ClOC—X—COCl   Formula (8)

Next, examples of fabricating the polyamide of the invention are illustrated. In the following, the invention is further illustrated in detail; however, the invention is not limited thereto.

Example 1

Synthesis of Polyamide (PA-1)

Firstly, 0.883 mmole of BABDPD is dissolved in 3.6 ml of N-methyl-2-pyrrolidinone (NMP) solvent. Next, 0.4 ml of propylene oxide is added into the mixture. Afterwards, 0.883 mmole of 4,4'-sulfonyldibenzoic acid chloride as a diacyl chloride monomer (i.e. Formula (5-1) as X group in the diacyl chloride compound shown in Formula (8)) are slowly added to the solution and reacted for 6 hours under room temperature. The solution is poured into a large amount of methanol for precipitation. The polymer is then washed with methanol and dried in a vacuum environment at 100° C. Finally, the polyamide (PA-1) is obtained.

Furthermore, identification and a property analysis of a chemical structure of the polyamide (PA-1) are illustrated below.

Relative viscosity: the relative viscosity in N,N-dimethylacetamide (DMAc) is 1.3 (a solution concentration of 0.5 g dL$^{-1}$ and a measuring temperature of 30° C.).

Solubility: soluble in solvents such as NMP, pyridine, tetrahydrofuran (THF), DMAc, dimethyl sulfoxide (DMSO), cyclohexanone, and so on.

Thin film mechanical property: a tensile strength is 35-66 MPa; an elongation is 2.1-7.6%; a tensile coefficient is 2.1-2.8 GPa.

Figure 8:
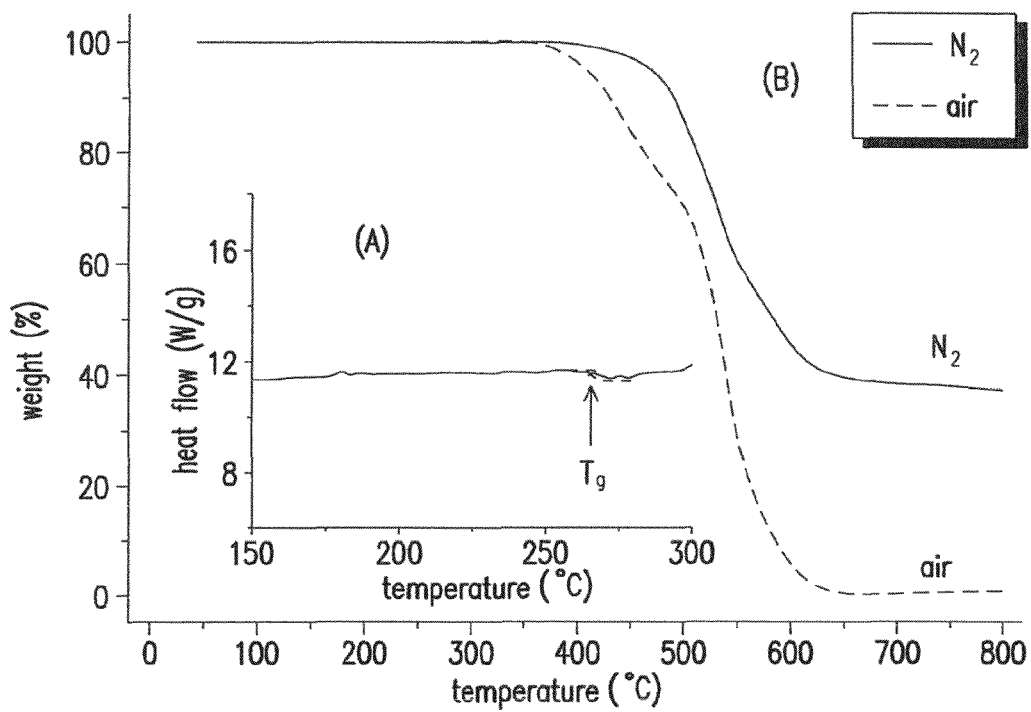
FIG. 8 is schematic diagrams illustrating results of glass transition temperature (Tg) of polyamide (PA-1) according to an example and showing a thermogravimetric analysis (TGA) of the polyamide (PA-1) under nitrogen ($N_2$) and under air.

FIG. 8 is schematic diagrams illustrating (A) results of glass transition temperature (Tg) of the polyamide (PA-1) in this example obtained using a differential scanning calorimeter (DSC), and (B) thermogravimetric analysis (TGA) of the polyamide (PA-1) of the present example under nitrogen and under air.

Thermal property: as shown in FIG. 8 (A), a glass transition temperature (Tg) is higher than 250° C.; as shown in FIG. 8 (B), in a TGA measurement in nitrogen, a temperature for 10% decomposition of the polyamide (PA-1) is 493° C., and in a TGA measurement in air, a temperature for 10% decomposition of the polyamide (PA-1) is 435° C.

Figure 9:
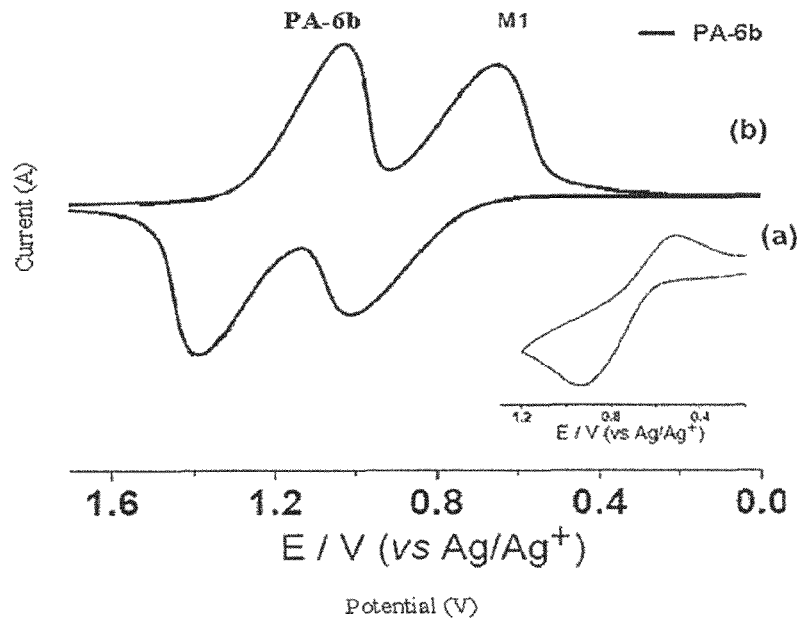
FIG. 9 is a schematic diagram showing a property research result of the polyamide (PA-1) according to an example using cyclic voltammetry (CV).

FIG. 9 is a schematic diagram showing a property research result of the polyamide (PA-1) of the present example using cyclic voltammetry (CV).

The CV diagram in FIG. 9 shows electrochemical properties of the polyamide (PA-1), and the electrochemical properties are illustrated in the following. Electrochemical property: oxidation half potential are respectively 0.82 V and 1.21 V; highest occupied molecular orbital (HOMO)=4.95 eV; lowest unoccupied molecular orbital (LUMO)=2.34 eV; band gap=2.61 eV.

Figure 10:
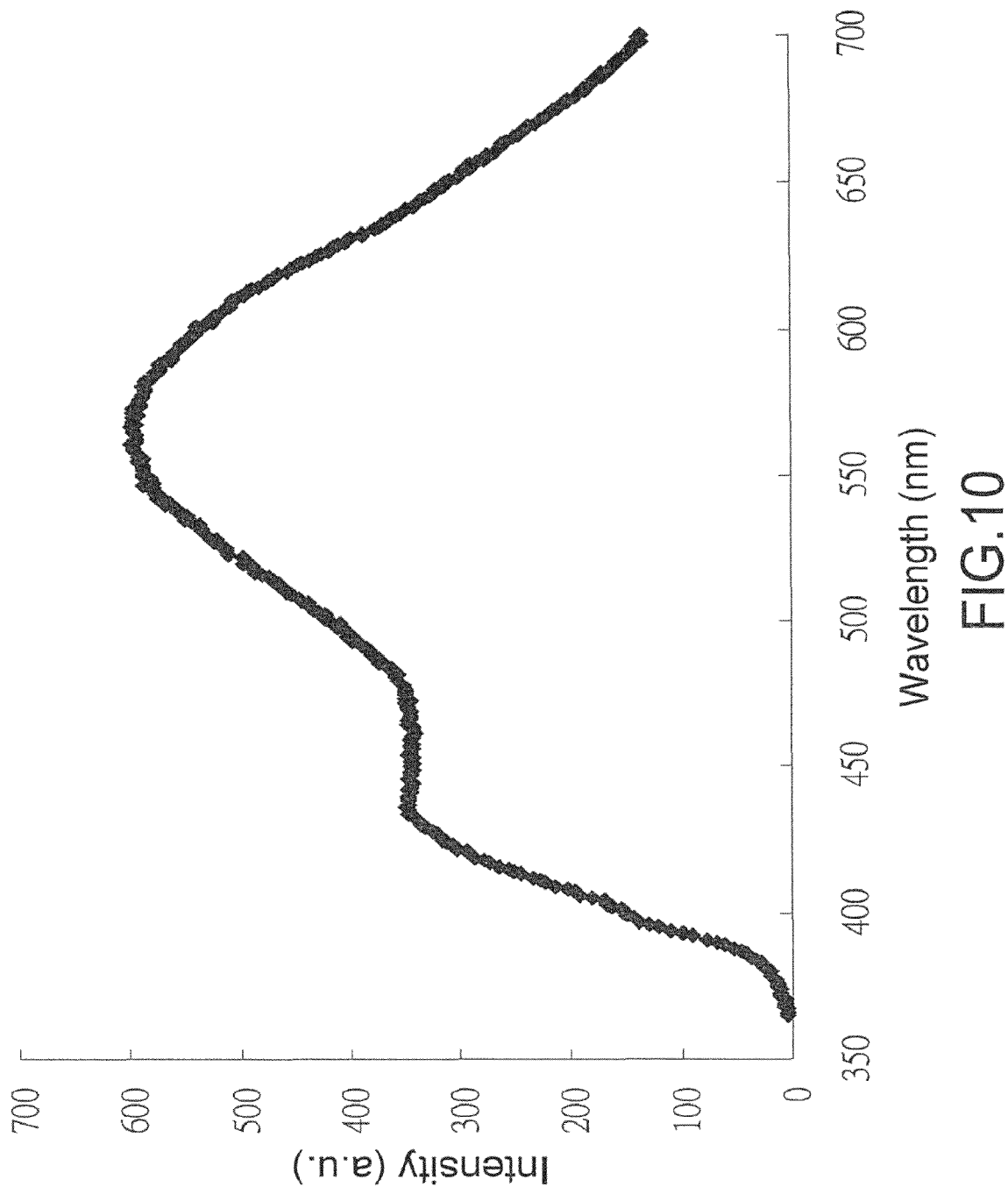
FIG. 10 is a schematic diagram of a luminescent spectrum of phosphorescence excitation of the polyamide (PA-1) according to an example.

FIG. 10 is a schematic diagram of a luminescent spectrum of phosphorescence excitation of the polyamide (PA-1) according to the present example.

In the present example, a UV-visible light is used to measure a largest absorption wavelength of the polyamide (PA-1). A light of this wavelength is used to excite the polyamide (PA-1), and a result thereof is shown in FIG. 10. The largest luminescence wavelength of the phosphorescence excitation is 560 nm.

Figure 11:
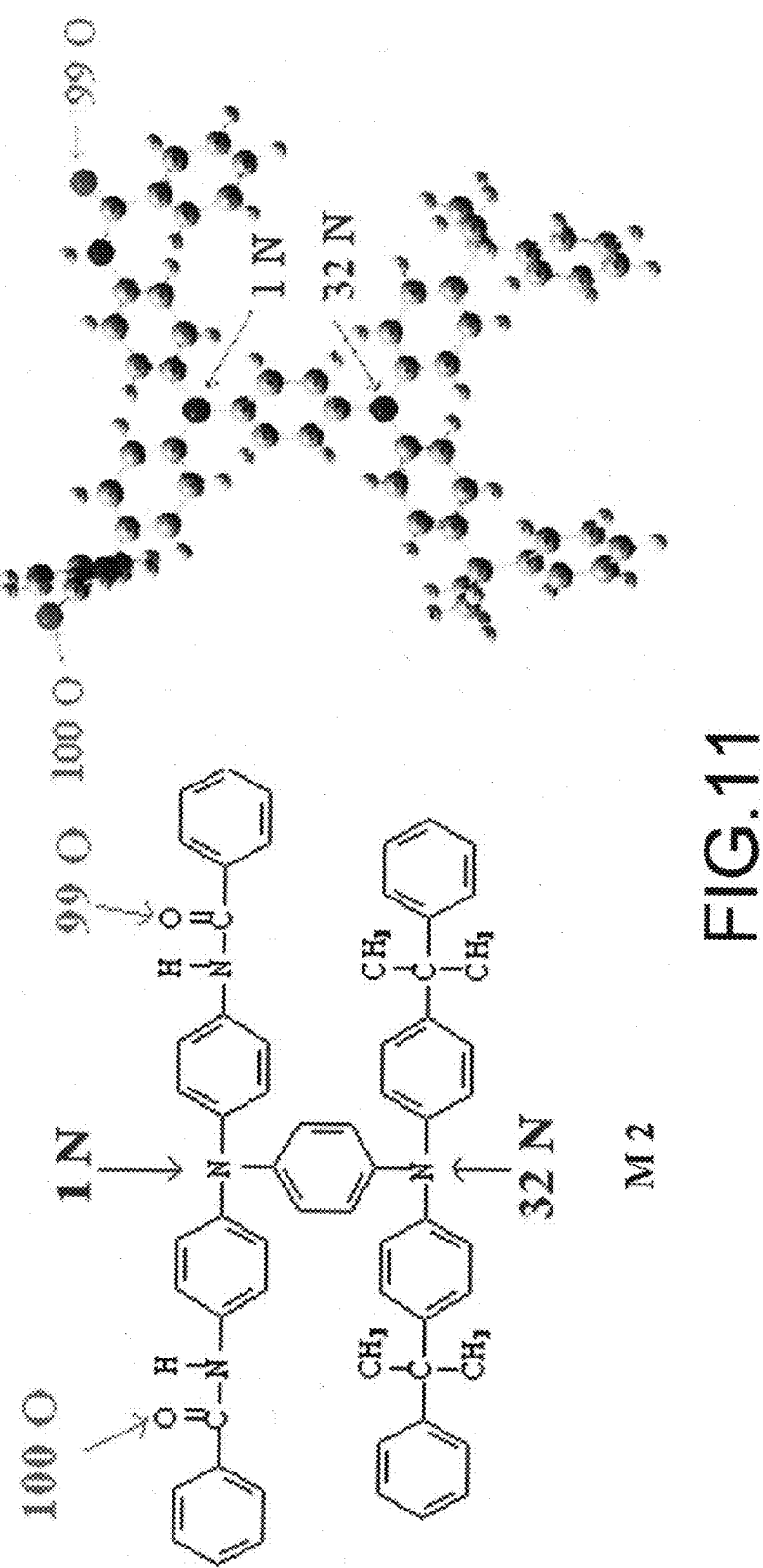
FIGS. 11 and 12 respectively illustrate a structure and electron density distribution contours of a unit polyamide (M2).
Figure 12:
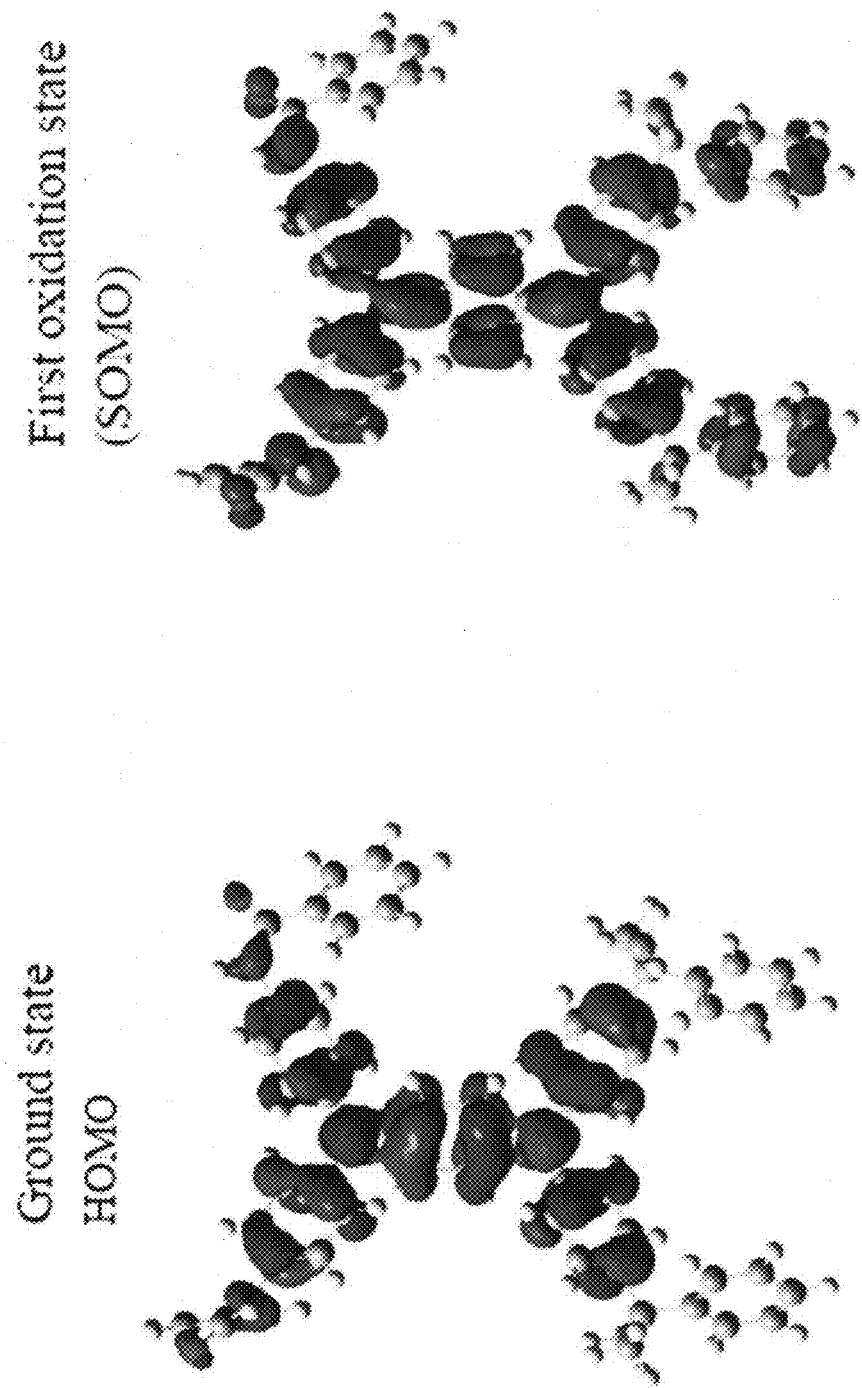

FIG. 11 illustrates a structure of a unit polyamide (M2) computed by the Gaussian 03 Software (DFT/B3LYP/6-31G (d)). FIG. 12 shows a ground state and a single occupied molecular orbital (SOMO) electron density distribution contours of a unit polyamide (M2) calculated with the Gaussian 03 Software (DFT/B3LYP/6-31G(d)).

As shown in FIGS. 11 and 12, in the present example, an oxidation mechanism (theoretical calculation) of the polyamide (M2) can be calculated using the Gaussian 03 Software (DFT/B3LYP/6-31G(d). For the first oxidation state (losing the first electron), 1 N, 32 N, 99 C, and 100 C atoms respectively contribute 4.0%, 3.2%, 2.6%, and 2.9% of electrons. For the second oxidation state (losing the second electron), 1 N, 9 C, 29 C, and 32 N atoms respectively contribute 1.3%, 2.1%, 2.6%, and 2.4% of electrons. The electron density contours of the ground state and the first oxidation state are included in FIG. 12.

Based on the new oxidation mechanism obtained from the molecular orbital theoretical calculation, it is suggested that the first electron removed from the HOMO of the molecule and the second electron removed from the SOMO of the molecule are not only the lone pair electrons on the nitrogen atom, but are contributed from all of the atoms inside the molecule.

Figure 13:
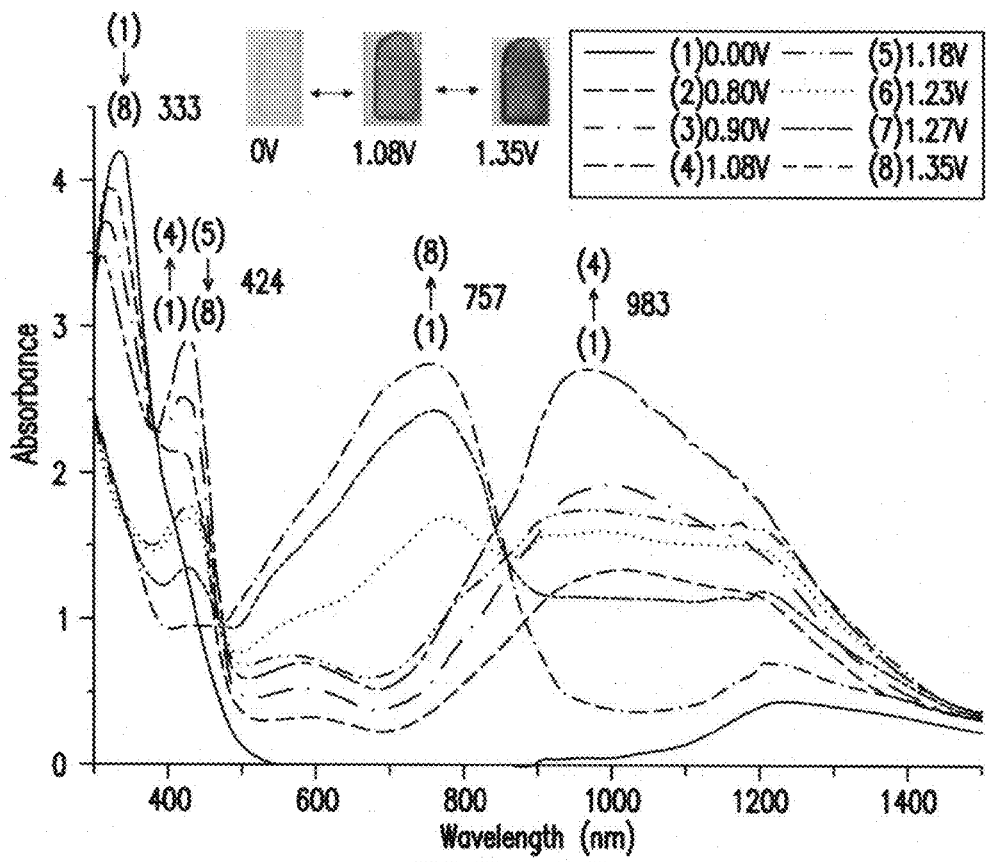
FIG. 13 shows absorption spectrum changes of the polyamide (PA-1) in UV-visible light measurement after electrochromism.

FIG. 13 shows absorption spectrum changes of PA-1 in UV-visible light measurement after electrochromism.

As illustrated in FIG. 13, in the present example (PA-1), when the potential increases from 0 V to 1.08 V (the first oxidation potential), the absorption of the UV-visible light spectrum at 333 nm decreases gradually, and new absorption peaks are generated at 424 nm and 983 nm. When the potential increases from 1.08 V to 1.35 V (the second oxidation potential), the absorptions of the UV-visible light spectrums at 424 nm and 983 nm decrease gradually, and a new peak is generated at 757 nm. At the same time, the polyamide (PA-1) thin film changes from pale yellow into green as the potential increases from 0 V to 1.08 V (the first oxidation potential). Later, the polyamide (PA-1) thin film turns into blue as the potential increases to 1.35 V (the second oxidation potential).

Figure 14:
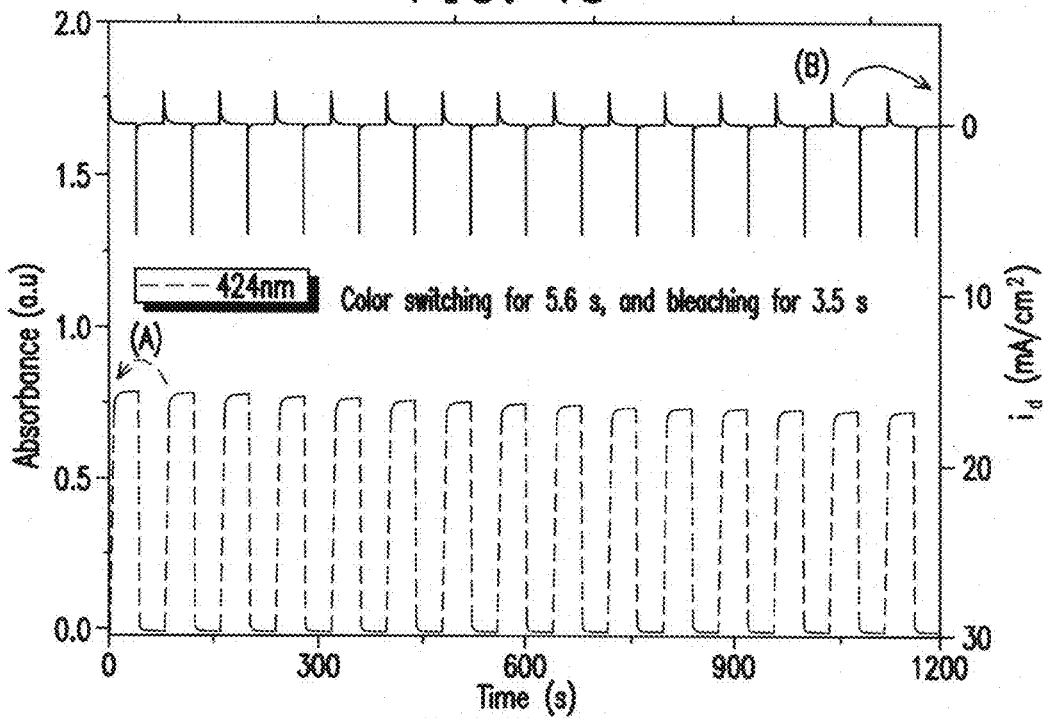
FIG. 14 illustrates (A) a UV-visible light spectrum of the polyamide (PA-1) measured in potential step under a fixed wavelength, and (B) a current consumption diagram of the polyamide (PA-1) in potential step.

FIG. 14 illustrates (A) a UV-visible light spectrum of the polyamide (PA-1) measured in potential step under a fixed wavelength, and (B) a current consumption diagram of the polyamide (PA-1) in potential step.

In the present example, an electrochromic switching time of the polyamide (PA-1) is calculated from the UV-visible light spectrum measured in the potential step at a fixed wavelength (as shown in FIG. 14). Here, the electrochromic switching time is defined as the time attaining 90% of the intensity variation of the absorption spectrum. The polyamide (PA-1) thin film in the present example under the UV-visible light with the fixed $\lambda_{max}$=424 nm has an electrochromic switching time (color switching) of 5.6 second (s) (oxidation), while the reduction time (color bleaching) is only 3.5 s. This reveals that the rates of oxidation and reduction of PA-1 are not the same.

In addition, the polyamide (PA-1) obtained is identified using the $^1$H-NMR analysis of the NMR spectrum. In the NMR spectrum obtained, s represents a singlet, d represents a doublet, t represents a triplet, q represents a quartet, and m represents a multiplet.

$^1$H NMR (THF-dg): δ (ppm)=1.62 (s, 6H, $H_d$); 6.92-6.93 (d, 2H, $H_h$+$H_g$); 6.93-6.94 (d, 2H, $H_f$); 7.01-7.03 (d, 2H, $H_i$); 7.07-7.08 (m, 3H, $H_e$+$H_a$); 7.18-7.19 (d, 2H, $H_b$); 7.23-7.24 (d, 2H, $H_c$); 7.64-7.66 (d, 2H, $H_j$); 8.03-8.07 (m, 4H, $H_l$+$H_k$); 9.55 (amide-NH).

It should be noted that since the polyamide of the invention includes a bis-triphenylamide group, the polyamide therefore has superior solubility, high glass transition temperature and thermal stability. Furthermore, the polyamide possesses electrochemical properties and electrochromic properties. In details, the new polyamide containing bis-triphenylamide in the invention has high carrier mobility, low ionization potential, and a feature of forming thin films easily. In addition, the nitrogen atom at the center of the polyamide containing bis-triphenylamide has an oxidation-reduction (redox) ability and can therefore be applied in electrochromic material. As a consequence, the polyamide can be widely utilized in constructions of mirrors, indicators, electrochromic displays, smart windows, and so on.

Moreover, in the new polyamide containing bis-triphenylamide, the nitrogen atom at the center is easily oxidized such that electrons are lost. The polyamide can be thus used as a superior hole-transporting material. Hence, the polyamide containing bis-triphenylamide can also fabricate thin layers of hole-transporting material, so as to be applied in organic light emitting diodes (OLED), solar cells, photoreceptors, emitters, electro-luminescent elements, and so on.

In summary, the nitro compound, the amine compound, and the polyamide derived therefrom at least have a part or all of the advantages listed below:

1. The nitro compound, the amine compound, and the polyamide derived therefrom each includes a triphenylamide group. Therefore, the polyamide containing bis-triphenylamide has superior solubility, high glass transition temperature, and thermal stability. The polyamide can be processed easily and has a wide application.

2. The nitro compound, the amine compound, and the polyamide derived therefrom can provide properties required by the elements according to the application scope thereof. The polyamide containing bis-triphenylamide has electrochemical properties and can be applied in electrochemical materials.

Although the invention has been described with reference to the above embodiments, it is apparent to one of ordinary skill in the art that modifications to the described embodiments may be made without departing from the spirit of the invention. Accordingly, the scope of the invention is defined by the attached claims not by the above detailed descriptions.

What is claimed is:

1. A polyamide, fabricated by performing a polycondensation reaction with the amine compound of Formula (4) and an acid or an acid derivative shown in Formula (5) as monomers, and represented by Formula (6):

Formula (4)

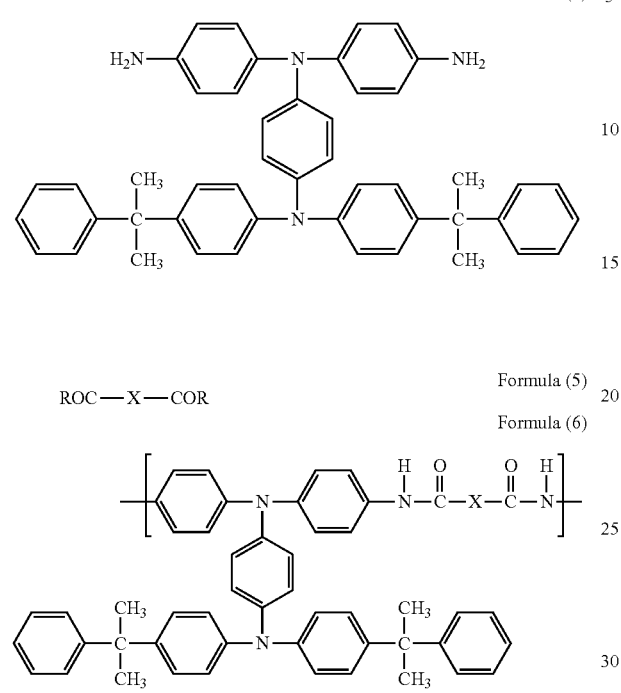

Formula (5)

ROC—X—COR

Formula (6)

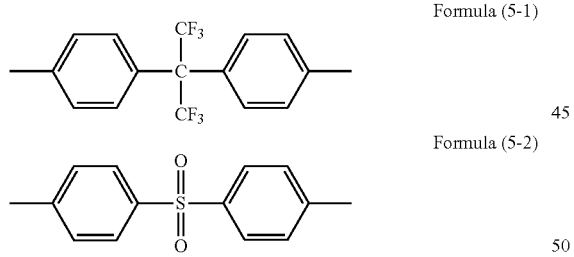

wherein X represents an aromatic group or an aliphatic group in Formula (5) and Formula (6), wherein in Formula (5), R represents an OH group or a halogen.

2. The polyamide as claimed in claim 1, wherein in Formula (5) and Formula (6), X represents a group selected from Formula (5-1) to Formula (5-11)

Formula (5-1)

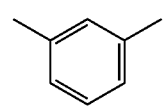

Formula (5-2)

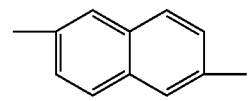

Formula (5-3)

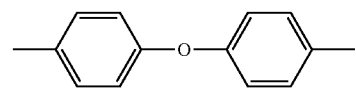

Formula (5-4)

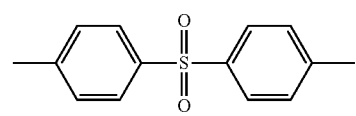

Formula (5-5)

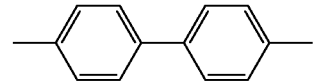

Formula (5-6)

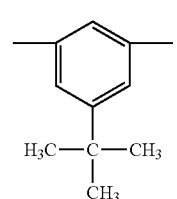

Formula (5-7)

Formula (5-8)

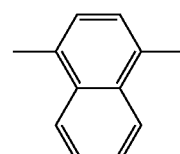

Formula (5-9)

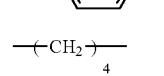

Formula (5-10)

—(CH$_2$)$_4$—

Formula (5-11)

3. The polyamide as claimed in claim 1, wherein the halogen is chlorine.

* * * * *